US012797428B2

(12) United States Patent
Farkas

(10) Patent No.: US 12,797,428 B2
(45) Date of Patent: Nov. 17, 2026

(54) COMPOSITION USED AS A MOOD-REGULATING STIMULANT

(71) Applicant: HAPPYGUM G.M.B.H., Vienna (AT)

(72) Inventor: Tim Farkas, Vienna (AT)

(73) Assignee: HAPPYGUM G.M.B.H., Vienna (AT)

( * ) Notice: Subject to any disclaimer, the term of this patent is extended or adjusted under 35 U.S.C. 154(b) by 788 days.

(21) Appl. No.: 18/014,168

(22) PCT Filed: Jul. 1, 2021

(86) PCT No.: PCT/IB2021/055934

§ 371 (c)(1),
(2) Date: Jan. 2, 2023

(87) PCT Pub. No.: WO2022/003630

PCT Pub. Date: Jan. 6, 2022

(65) Prior Publication Data

US 2023/0330170 A1 Oct. 19, 2023

(30) Foreign Application Priority Data

Jul. 1, 2020 (DE) ..................... 10 2020 117 395.4

(51) Int. Cl.

*A61K 36/53* (2006.01)
*A61K 9/68* (2006.01)
*A61K 47/12* (2006.01)
*A61K 47/22* (2006.01)

(52) U.S. Cl.

CPC ............ *A61K 36/53* (2013.01); *A61K 9/0058* (2013.01); *A61K 47/12* (2013.01); *A61K 47/22* (2013.01)

(58) Field of Classification Search

CPC ...... A61K 36/53; A61K 9/0058; A61K 47/12; A61K 47/22; A61K 47/26; A61K 47/02; A61P 1/00; A61P 25/00; A61P 25/22
See application file for complete search history.

(56) References Cited

U.S. PATENT DOCUMENTS

2008/0008663 A1* 1/2008 Leveille ................ A61K 36/23
424/746

FOREIGN PATENT DOCUMENTS

EP 1623716 2/2006
EP 2219467 8/2010

OTHER PUBLICATIONS

English Translation of Specification for EP1623716A1 from IDS filed Jan. 2, 2023 (Year: 2006).*
International Search Report of PCT/IB2021/055934.
Written Opinion of PCT/IB2021/055934.

* cited by examiner

*Primary Examiner* — Robert A Wax
*Assistant Examiner* — Quanglong N Truong

(57) ABSTRACT

Disclosed is a composition used as a mood-regulating stimulant comprising a gum base which contains 0.1 to 1 wt % of lavender oil.

17 Claims, 8 Drawing Sheets

COMPOSITION USED AS A MOOD-REGULATING STIMULANT

CROSS-REFERENCE TO RELATED APPLICATIONS

This application is a national stage application of PCT/162021/055934. This application claims priorities from PCT Application No. PCT/162021/055934, filed Jul. 1, 2021, and from the Germany patent application 10 2020 117 395.4 filed Jul. 1, 2020, the content of which are incorporated herein in the entirety by reference.

TECHNICAL FIELD

The present disclosure relates to a composition used as a mood-regulating stimulant.

BACKGROUND

From Uehleke, B., et al, "Phase II trial on the effects of Silexan in patients with neurasthenia, post-traumatic stress disorder or somatization disorder", Phytomedicine, year 2012, issue 19, page 665 to 671 is known to use lavender as an antidepressant with sedative and anxiolytic effects and therefore also as a sedative.

It is the object of the disclosure to specify another use of lavender.

According to one aspect of the disclosure, a composition comprises lavender oil as active ingredient for medicinal use in a treatment of a concentration disorder or attention deficit disorder, (ADD) and a gum base, characterized in that the composition comprises the gum base, and lavender oil as active ingredient in a concentration of 0.1 to 1 wt %, preferably of 0.2 to 0.4 wt %, more preferably of 0.3 wt %.

Based on trials, it has been found that lavender oil can also be used as a stimulant. The effect is therefore reversed to an antidepressant with sedative and anxiolytic effect, activates cognition and eliminates fatigue.

However, lavender taken orally shows adverse effects, such as gastrointestinal disorders in the form of dyspepsia and nausea. Allergic reactions are also known.

Especially against concentration disorders, users tend to take a potential active ingredient frequently and in high doses throughout the day, which further increases the adverse effects mentioned above.

SUMMARY

For the use of lavender as a mood-regulating stimulant, the present disclosure therefore proposes an administration in chewing gum form, so that the lavender oil is absorbed buccally or sublingually. Here, it has been verified through trials that the aforementioned cognition enhancing and fatigue eliminating effect can be achieved with even a significantly smaller quantity of lavender compared to other dosage forms, such as capsules or tablets.

In one embodiment of the composition, lavender oil is the only active ingredient.

In another embodiment of the composition, the gum base has a tensile strength between 0.25 $N/mm^2$ and 4 $N/mm^2$ for using the facial muscles.

In still another embodiment, the gum base has synthetic and/or natural gum as a consistency former.

In one embodiment of the specified chewing gum, the amount of lavender oil is between 0.2 wt % and 0.4 wt %. During buccal and sublingual administration, a significantly higher concentration of lavender oil enters the bloodstream, which is further stimulated by chewing. With a proportion of lavender oil of 0.3 wt %, an optimal effect can be achieved.

In an additional embodiment of the specified disclosure, the specified composition further comprises 0.05 to 0.5 wt %, preferably 0.08 to 0.2 wt %, particularly preferred 0.1 wt % of a trace element. In particular, the trace element zinc supports the regeneration of the oral mucosa and, in the case of a longer-term intake of the specified composition, ensures that the lavender oil released during chewing of the chewing gum mass can be optimally absorbed via the oral mucosa.

In an additional embodiment of the specified disclosure, the specified composition comprises 0.1 wt % to 1 wt %, preferably 0.15 wt % to 0.35 wt %, particularly preferred 0.25 wt % of a salt. Salts such as sodium chloride salt have an antibacterial, disinfecting, soothing, decongestant and anti-inflammatory effect on the oral mucosa. This reduces bacteria in the mouth and prevents inflammation and infection. Salts also moisten the irritated and dried mucous membranes in the case of an inflammation of the throat, which are thus supported in their function. In addition, salts have a cleansing and circulation-boosting effect. Coatings and mucus are loosened from the mucous membranes, so that a regeneration of the gums occurs. In this way, the absorption of the lavender oil through the oral mucosa is further improved, can optional.

In a further embodiment, the specified composition further comprises 0.05 wt % to 0.5 wt %, preferably 0.09 wt % to 0.3 wt %, more preferably 0.15 wt % of a vitamin B. Vitamin B, such as pantothenic acid and niacin, contribute to the preservation of the oral mucosa and thus ensure the effective absorption of the lavender oil when the specified composition is taken for a longer period of time.

In a further embodiment, the specified composition further comprises 0.1 wt % to 1 wt %, preferably 0.2 wt % to 0.4 wt %, particularly preferred 0.3 wt % of a vitamin D. Vitamin D, such as biotin, contributes to the preservation of the oral mucosa and thus ensures the effective absorption of the lavender oil when the specified composition is taken for a longer period of time.

In a particular embodiment, the specified composition further comprises an acidity regulator. The acidity regulator can be used to adjust saliva generation in the oral cavity and thus further improves the condition for the absorption of the lavender oil via the oral mucosa. For this purpose, citric acid has been found to be the most suitable acidity regulator.

In another embodiment of the specified composition, the gum base comprises between 50 wt % and 99 wt %, preferably between 70 wt % and 80 wt %, particularly preferred 75 wt % of a sugar alcohol or a mixture of sugar alcohols, such as sorbitol, mannitol, isomalt, maltitol, lactitol, xylitol, erythritol, polyglycitol syrup. Sugar alcohols have a slightly cooling effect in the oral cavity, which also has a positive effect on the buccal or sublingual absorption of the lavender oil.

BRIEF DESCRIPTION OF THE DRAWINGS

The above-described properties, features and advantages of this disclosure, as well as the manner in which they are achieved, will become clearer in connection with the following description of the embodiments, which are explained in more detail in connection with the drawing, in which.

DETAILED DESCRIPTION

Figure 1:
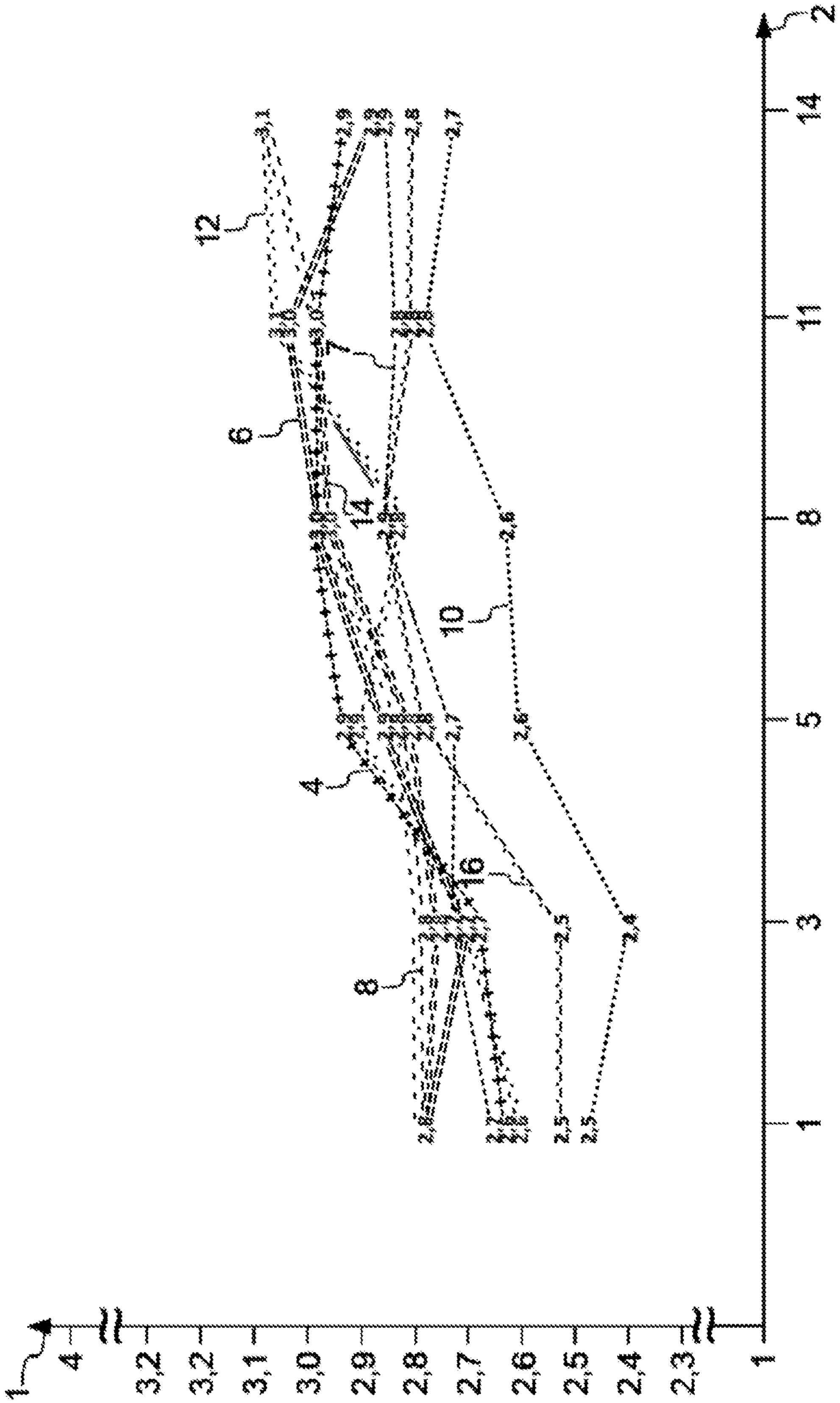
FIG. 1 is a diagram with mean values plotted over time on positively connoted moods of subjects who took a composition according to the disclosure, according to the Brief Mood Introspection Scale, abbreviated BMIS, 3rd edition, Feb. 26, 2019.

In the figures, the same technical elements are provided with the same reference signs, and are only described once.

The efficacy of the claimed composition was determined using an embodiment example of the claimed composition in a clinical trial and compared to an alternative composition.

The embodiment example of the claimed composition was a plurality of chewing gums of 2 g each. Each chewing gum contained 1.5 g of a sugar alcohol blend of sorbitol, maltiol and mannitol, a vitamin and mineral blend of 5 mg of salt, 2 mg of zinc, 2 mg of niacin, 0.8 mg of pantothenic acid and 6.5 μg of biotin. Furthermore, 2 mg of citric acid and 6 mg of lavender oil were added to the composition. The rest of each chewing gum were emollients, humectants, antioxidants, flavors, colorants and emulsifiers, which add nothing to the claimed effect of the composition.

The alternative composition was a variety of tablets. Each tablet contained 50 mg of lavender flower extract, 10 mg of lavender oil, 1.1 mg of vitamin B1, 1.4 mg of vitamin B2, 6 mg of pantothenic acid, 1.4 mg of vitamin B6 and 5 μg of vitamin B12, such as those sold by Queisser Pharma GmbH & Co. KG under the trade name Doppelherz aktiv Lavendel.

Each tablet of the alternative composition therefore contained approximately twice the lavender extract compared to a chewing gum according to the embodiment example of the claimed composition.

To collect the clinical trial data, 80 subjects were divided into a group of 40 subjects for taking the chewing gums according to the embodiment example of the claimed composition and a group of 40 subjects for taking the tablets according to the alternative composition. Depending on the group, the subject took one chewing gum according to the embodiment example of the claimed composition or two tablets according to the alternative composition twice a day over a period of 14 days.

To collect the trial data, the subjects filled out a questionnaire according to the Brief Mood Introspection Scale, abbreviated BMIS, 3rd edition, Feb. 26, 2019, on the first day, the third day, the fifth day, the eighth day, the eleventh day, and the fourteenth day, respectively, with which they provided information about their mood on various scales.

With each questionnaire, a subject's mood was assessed on sixteen different mood scales. The individual mood scales are defined by the BMIS and a mood scale with which is asked how lively (in BMIS: "Lively") the subject feels, a mood scale how happy (in BMIS: "Happy") the subject feels, a mood scale how sad (in BMIS: "Sad") the subject feels, a mood scale how tired (in BMIS: "Tired") the subject feels, a mood scale how caring (in BMIS: "Caring") the subject feels, a mood scale how content (in BMIS: "Content") the subject feels, a mood scale how gloomy (in BMIS: "Gloomy") the subject feels, a mood scale how jittery (in BMIS: "Jittery") the subject feels, a mood scale how drowsy (in BMIS: "Drowsy") the subject feels, a mood scale how grouchy (in BMIS: "Grouchy") the subject feels, a mood scale how peppy (in BMIS: "Peppy") the subject feels, a mood scale how nervous (in BMIS: "Nervous") the subject feels, a mood scale how calm (in BMIS: "Calm") the subject feels, a mood scale how loving (in BMIS: "Loving") the subject feels, a mood scale how fed up (in BMIS: "Fed up") the subject feels, a mood scale how active (in BMIS: "Active") the subject feels.

On each scale, the subject could decide whether the mood of the corresponding scale certainly applied to him, whether the mood of the corresponding scale probably applied to him, whether the mood of the corresponding scale probably did not apply to him, or whether the mood of the corresponding scale certainly did not apply to him. If the mood was certainly true for the subject, the subject's decision was assigned a value of 4. If the mood was probably true for the subject, the subject's decision was assigned a value of 3. If the mood was probably not true for the subject, the subject's decision was assigned a value of 2. If the mood was certainly not true for the subject, the subject's decision was assigned a value of 1.

The questionnaires were analyzed by first averaging across all participants for each group for each day and for each scale.

Table 1 below shows the result of this averaging for the group to whom the chewing gums were administered according to the embodiment example of the claimed composition:

TABLE 1

| | Day 1 | Day 3 | Day 5 | Day 8 | Day | Day 14 |
|---|---|---|---|---|---|---|
| Lively | 2.63 | 2.68 | 2.93 | 2.98 | 2.98 | 2.93 |
| Happy | 2.78 | 2.70 | 2.85 | 2.97 | 3.03 | 2.88 |
| Sad | 1.80 | 2.03 | 1.93 | 1.83 | 1.68 | 1.80 |
| Tired | 2.48 | 2.38 | 2.15 | 2.08 | 2.15 | 2.08 |
| Caring | 2.65 | 2.73 | 2.73 | 2.85 | 2.83 | 2.85 |
| Content | 2.78 | 2.78 | 2.83 | 2.95 | 2.98 | 3.08 |
| Gloomy | 1.90 | 2.00 | 1.80 | 1.78 | 1.83 | 1.65 |
| Jittery | 1.63 | 1.55 | 1.73 | 1.63 | 1.55 | 1.60 |
| Drowsy | 2.20 | 2.38 | 2.10 | 2.05 | 2.03 | 2.08 |
| Grouchy | 1.63 | 1.65 | 1.70 | 1.50 | 1.68 | 1.55 |
| Peppy | 2.48 | 2.40 | 2.60 | 2.63 | 2.78 | 2.73 |
| Nervous | 1.93 | 2.03 | 1.60 | 1.70 | 1.75 | 1.65 |
| Calm | 2.60 | 2.70 | 2.90 | 2.83 | 3.05 | 3.08 |
| Loving | 2.78 | 2.75 | 2.80 | 2.95 | 2.98 | 2.93 |

TABLE 1-continued

| | Day 1 | Day 3 | Day 5 | Day 8 | Day | Day 14 |
|---|---|---|---|---|---|---|
| Fed up | 2.00 | 2.18 | 1.90 | 1.80 | 1.88 | 1.78 |
| Active | 2.53 | 2.53 | 2.78 | 2.85 | 2.80 | 2.80 |

In contrast, Table 2 below shows the result of the averaging for the group to whom the tablets were administered according to the alternative composition:

TABLE 2

| | Day 1 | Day 3 | Day 5 | Day 8 | Day 11 | Day 14 |
|---|---|---|---|---|---|---|
| Lively | 2.78 | 2.83 | 2.95 | 3.08 | 2.98 | 3.20 |
| Happy | 2.88 | 2.95 | 3.13 | 3.00 | 2.88 | 3.13 |
| Sad | 1.70 | 1.73 | 1.63 | 1.73 | 1.88 | 1.60 |
| Tired | 2.25 | 2.13 | 1.85 | 2.00 | 2.00 | 1.83 |
| Caring | 2.70 | 2.80 | 3.00 | 2.80 | 2.83 | 2.90 |
| Content | 2.88 | 2.95 | 3.18 | 3.25 | 2.98 | 3.15 |
| Gloomy | 1.63 | 1.75 | 1.75 | 1.68 | 1.73 | 1.65 |
| Jittery | 1.50 | 1.55 | 1.53 | 1.48 | 1.63 | 1.60 |
| Drowsy | 2.23 | 2.23 | 1.98 | 2.13 | 2.18 | 1.98 |
| Grouchy | 1.68 | 1.60 | 1.45 | 1.55 | 1.53 | 1.48 |
| Peppy | 2.58 | 2.60 | 2.78 | 2.75 | 2.55 | 2.78 |
| Nervous | 1.68 | 1.78 | 1.68 | 1.78 | 1.80 | 1.73 |
| Calm | 2.80 | 2.95 | 3.05 | 3.00 | 2.98 | 3.10 |
| Loving | 2.83 | 2.98 | 3.05 | 3.00 | 2.95 | 3.03 |
| Fed up | 1.90 | 1.80 | 1.80 | 1.89 | 1.80 | 1.76 |
| Active | 2.63 | 2.78 | 2.93 | 2.83 | 2.73 | 2.80 |

Figure 2:
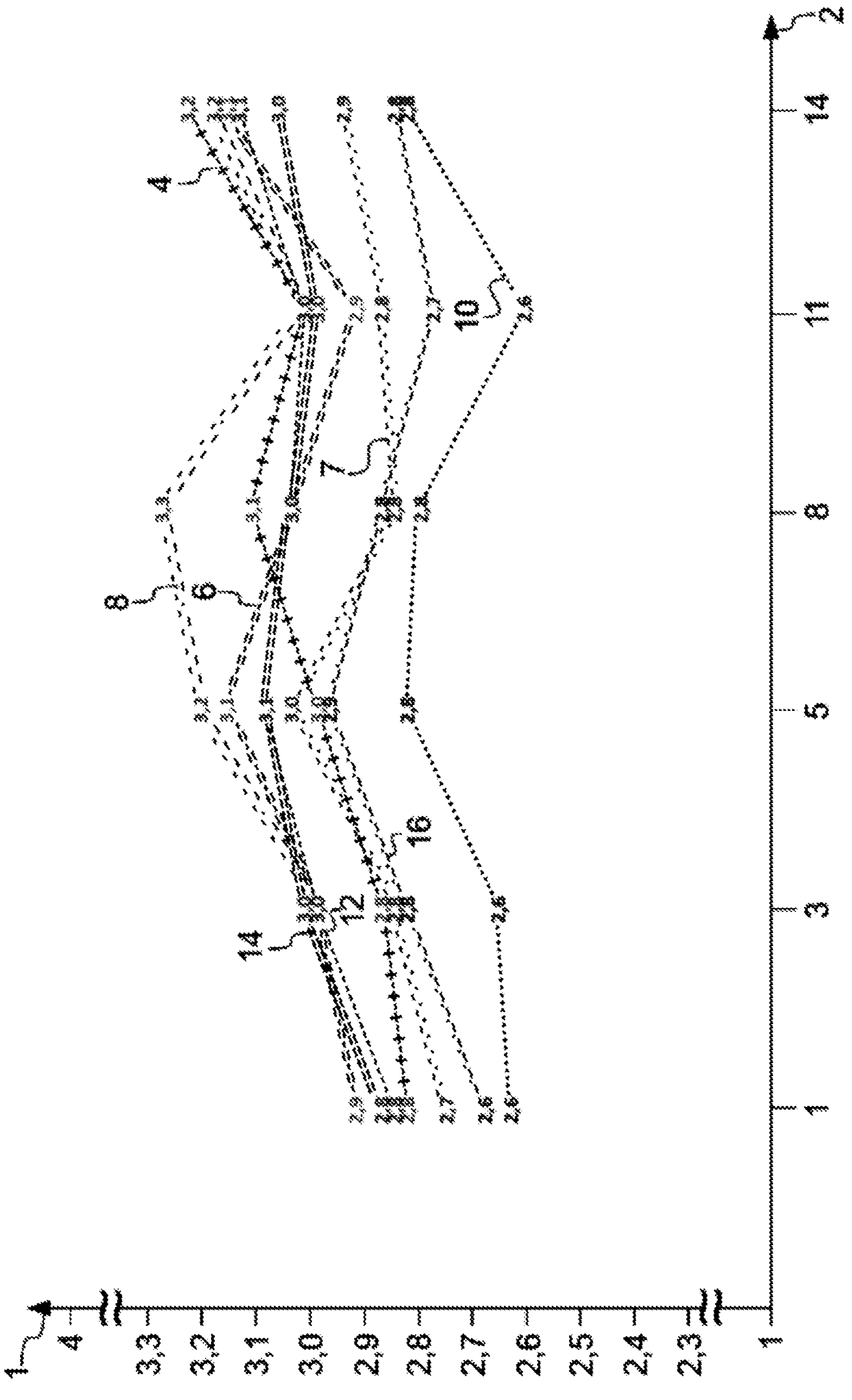
FIG. 2 is a diagram with mean values plotted over time on positively connoted moods of subjects who took an alternative composition, according to the Brief Mood Introspection Scale, abbreviated BMIS, 3rd edition, Feb. 26, 2019.

The values 1 from tables 1 and 2 are plotted against time 2 in FIGS. 1 to 4. FIG. 1 shows the values 1 of the positively connoted mood scales of table 1. These are the mood scales lively 4, happy 6, caring 7, content 8, peppy 10, calm 12, loving 14, and active 16. In FIG. 2, the same positively connoted mood scales are plotted, but from Table 2.

Figure 3:
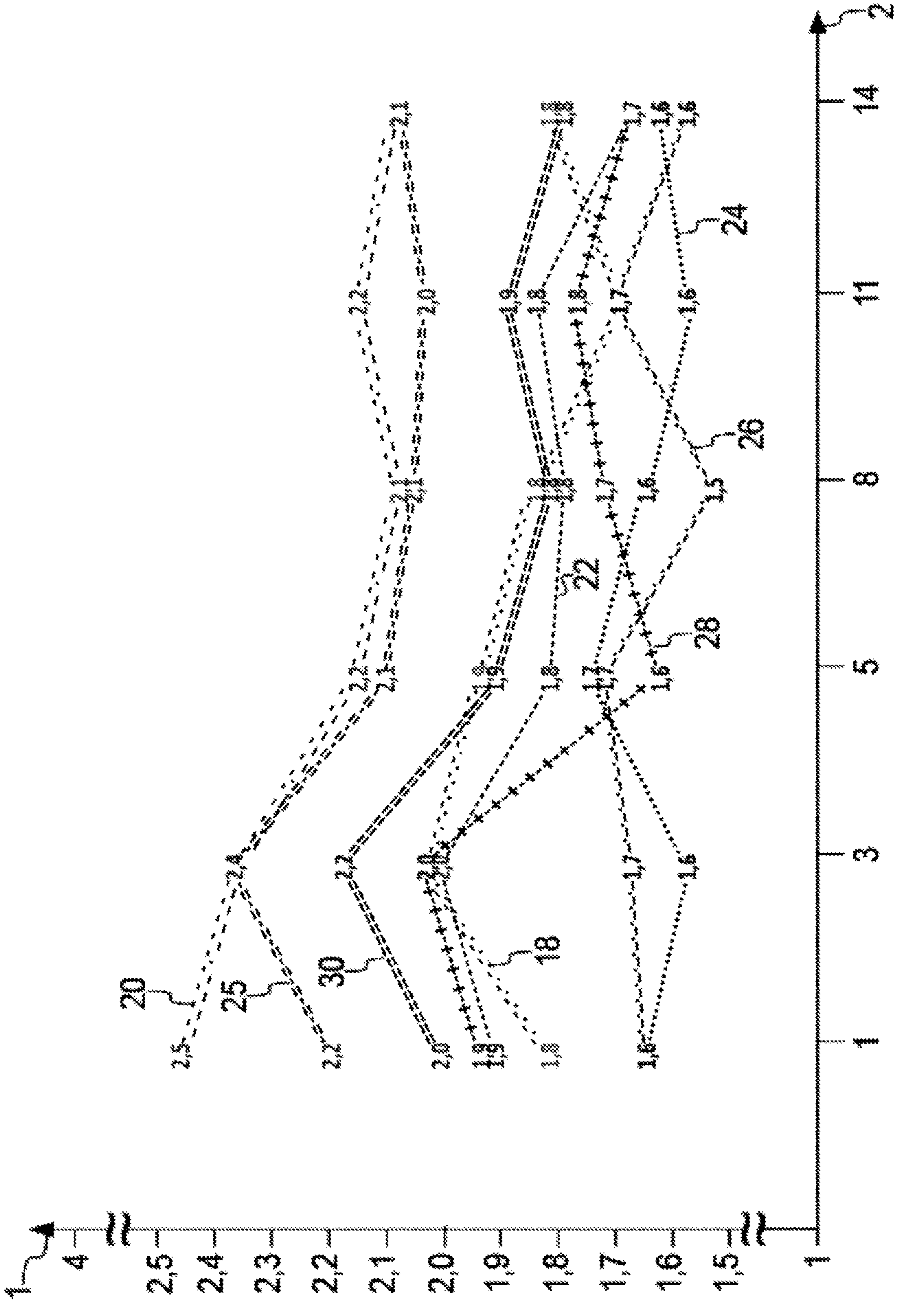
FIG. 3 is a diagram with mean values plotted over time on negatively connoted moods of subjects who took a composition according to the disclosure, according to the Brief Mood Introspection Scale, abbreviated BMIS, 3rd edition, Feb. 26, 2019.
Figure 4:
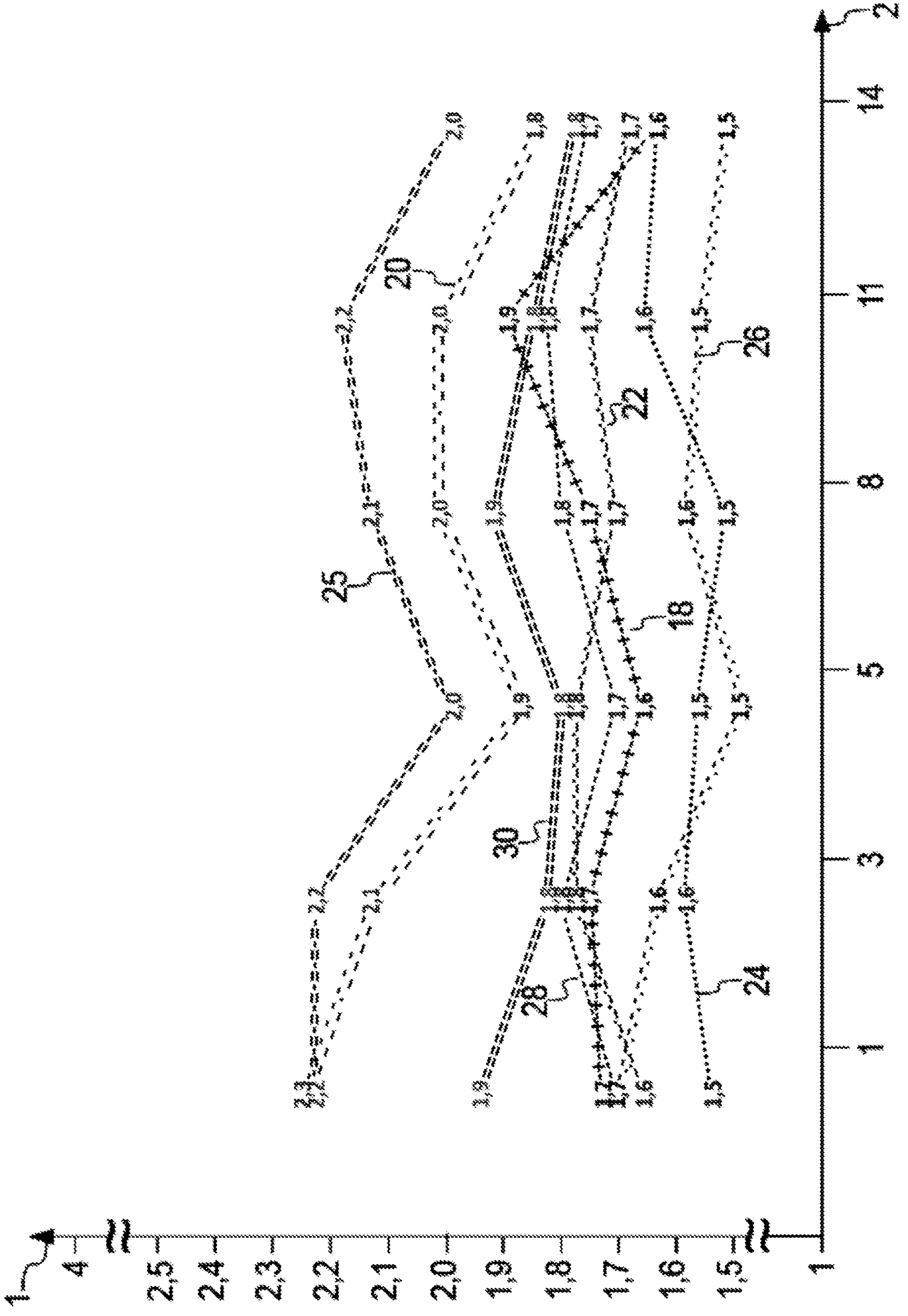
FIG. 4 is a diagram with mean values plotted over time on negatively connoted moods of subjects who took an alternative composition, according to the Brief Mood Introspection Scale, abbreviated BMIS, 3rd edition, Feb. 26, 2019.

FIG. 3 shows the values 1 of the negatively connoted mood scales of Table 1. These are the mood scales sad 18, tired 20, gloomy 22, jittery 24, drowsy 25, grouchy 26, nervous 28, and fed up 30. In FIG. 4, the same negatively connoted mood scales are plotted, but from Table 2.

FIGS. 1 and 2 show that all stimulating mood scales show a positive trend, both for the claimed composition and for the alternative composition. Significant in the single evaluation of the claimed composition is the mood scale calm 12 and of the alternative composition the mood scale lively 4. Pooling the subject groups of both compositions additionally results in a significant improvement for the mood scale satisfied 8.

The moods belonging to the mood scales in FIGS. 1 and 2 are perceived as pleasant and stimulating and positive, as shown in Table 1.1 of the Brief Mood Introspection Scale, abbreviated BMIS, 3rd edition, Feb. 26, 2019. It was possible to increase all of these positive moods either in trend or significantly with both the claimed composition and the alternative composition.

FIGS. 3 and 4 show that all inhibitory mood scales show a constant trend, both for the claimed composition and for the alternative composition. Significant in the individual evaluation is even a decreasing trend of fatigue 20 with the claimed composition, which is not so recognizable with the alternative composition. The subjects were more alert and able to concentrate better.

Then, for further evaluation, a value on the four subscales according to BMIS was calculated from the mean values for each day, i.e., a daily value on the satisfaction scale (according to BMIS: "Pleasant-Unpleasant"), a daily value on the arousal scale (according to BMIS: "Arousal-Calm"), a daily value on the fatigue scale (according to BMIS: "Positive-Tired"), and a daily value on the relaxation scale (according to BMIS: "Negative-Relaxed").

Table 3 below shows the values for the subscales for the group that was administered the chewing gums according to the embodiment example of the claimed composition:

TABLE 3

| | Day 1 | Day 3 | Day 5 | Day 8 | Day 11 | Day 14 |
|---|---|---|---|---|---|---|
| Pleasant - Unpleasant | 5.7 | 5.1 | 7.5 | 8.65 | 8.9 | 9.1 |
| Excited - Calm | 17.2 | 17.8 | 17.7 | 18.1 | 17.8 | 17.6 |
| Positive - Tired | 8.4 | 8.3 | 9.6 | 10.1 | 10.2 | 10.1 |
| Negative - Relaxed | 6.7 | 7.1 | 6.1 | 5.9 | 5.6 | 5.4 |

In contrast, Table 4 below shows the values for the subscales for the group that was administered the tablets according to the alternative composition:

TABLE 4

| | Day 1 | Day 3 | Day 5 | Day 8 | Day 11 | Day 14 |
|---|---|---|---|---|---|---|
| Pleasant - Unpleasant | 7.5 | 8.3 | 10.4 | 9.5 | 8.3 | 10.5 |
| Excited - Calm | 16.9 | 17.5 | 18.2 | 18.0 | 17.9 | 18.1 |
| Positive - Tired | 9.0 | 9.6 | 10.9 | 10.3 | 9.9 | 10.9 |
| Negative - Relaxed | 5.6 | 5.7 | 5.3 | 5.6 | 5.9 | 5.2 |

Figure 5:
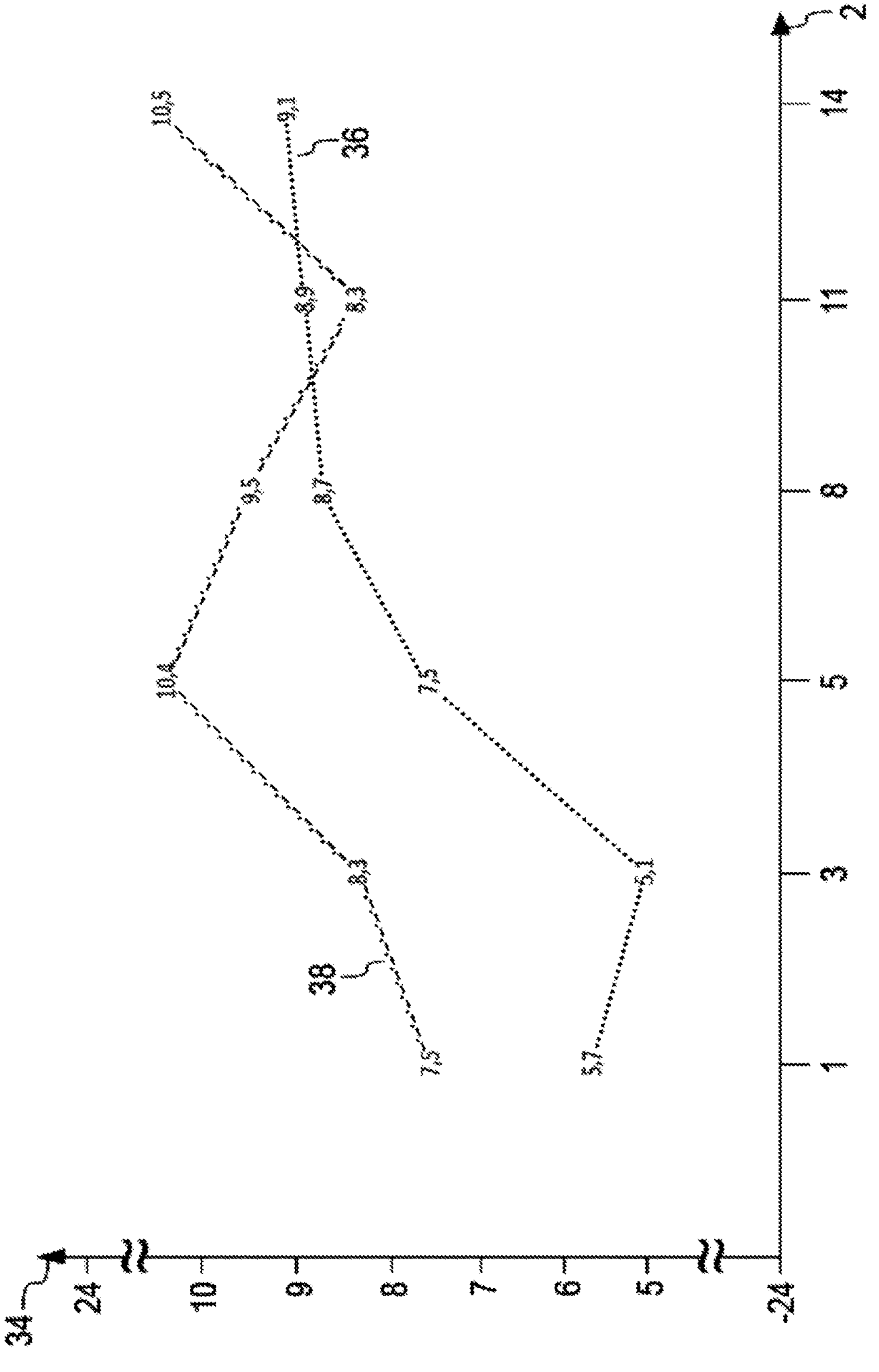
FIG. 5 is a diagram showing an evaluation of collected trial data on the "Pleasant-Unpleasant" scale according to the Brief Mood Introspection Scale, abbreviated BMIS, 3rd edition, Feb. 26, 2019.
Figure 6:
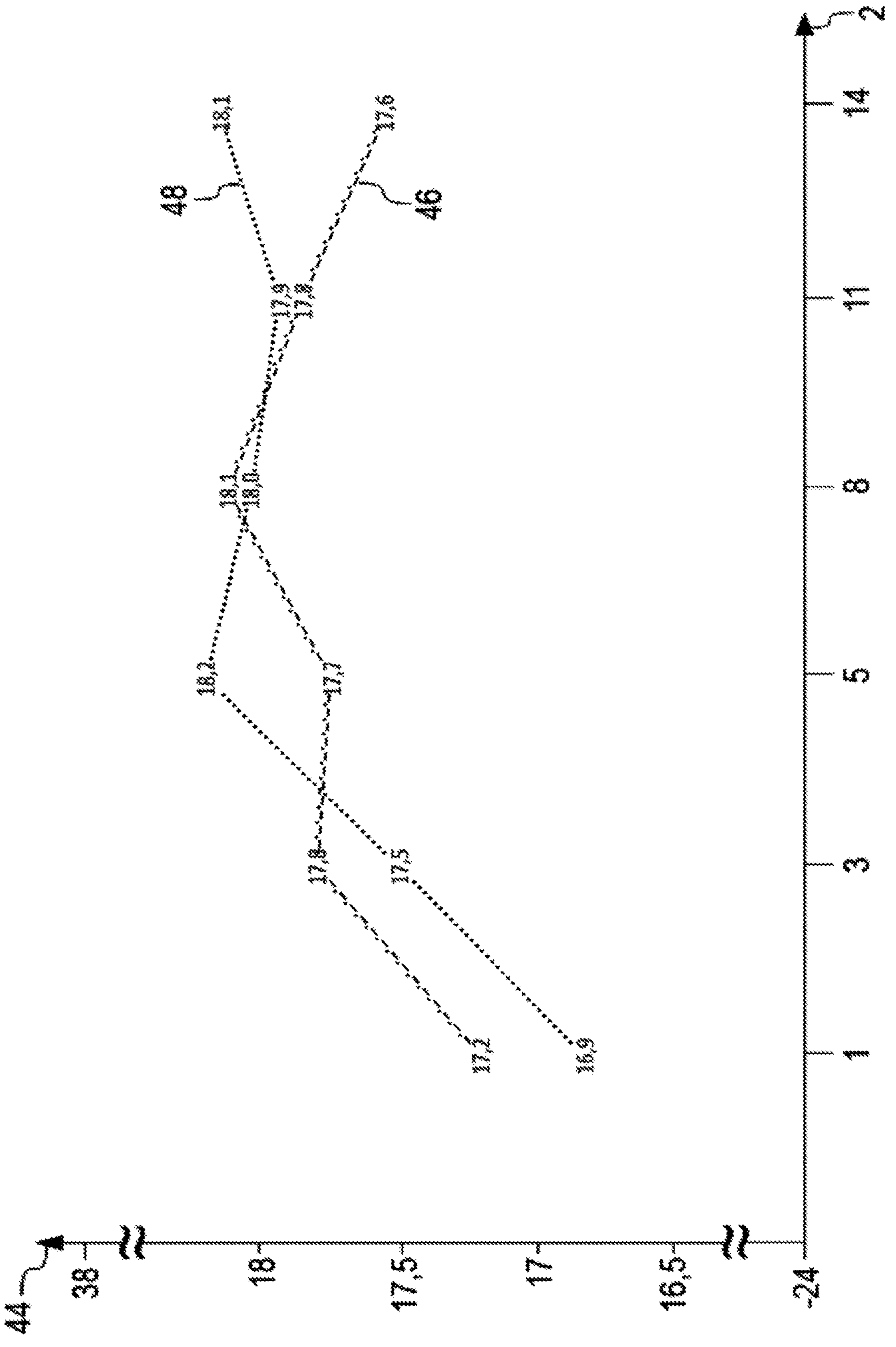
FIG. 6 is a diagram showing an evaluation of collected trial data on the "Excited-Calm" scale according to the Brief Mood Introspection Scale, abbreviated BMIS, 3rd edition, Feb. 26, 2019.
Figure 7:
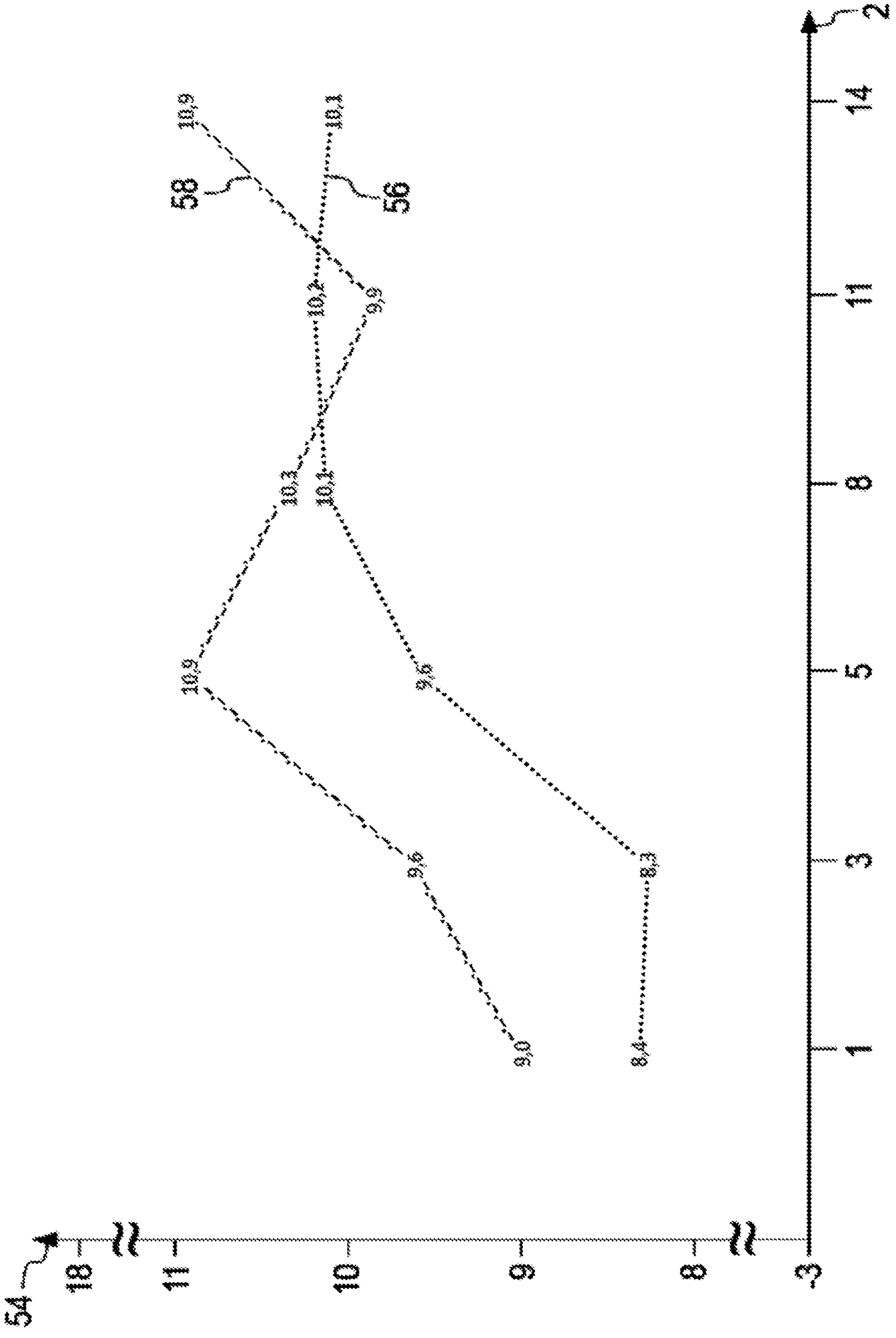
FIG. 7 is a diagram showing an evaluation of collected trial data on the "Positive-Tired" scale according to the Brief Mood Introspection Scale, abbreviated BMIS, 3rd edition, Feb. 26, 2019.
Figure 8:
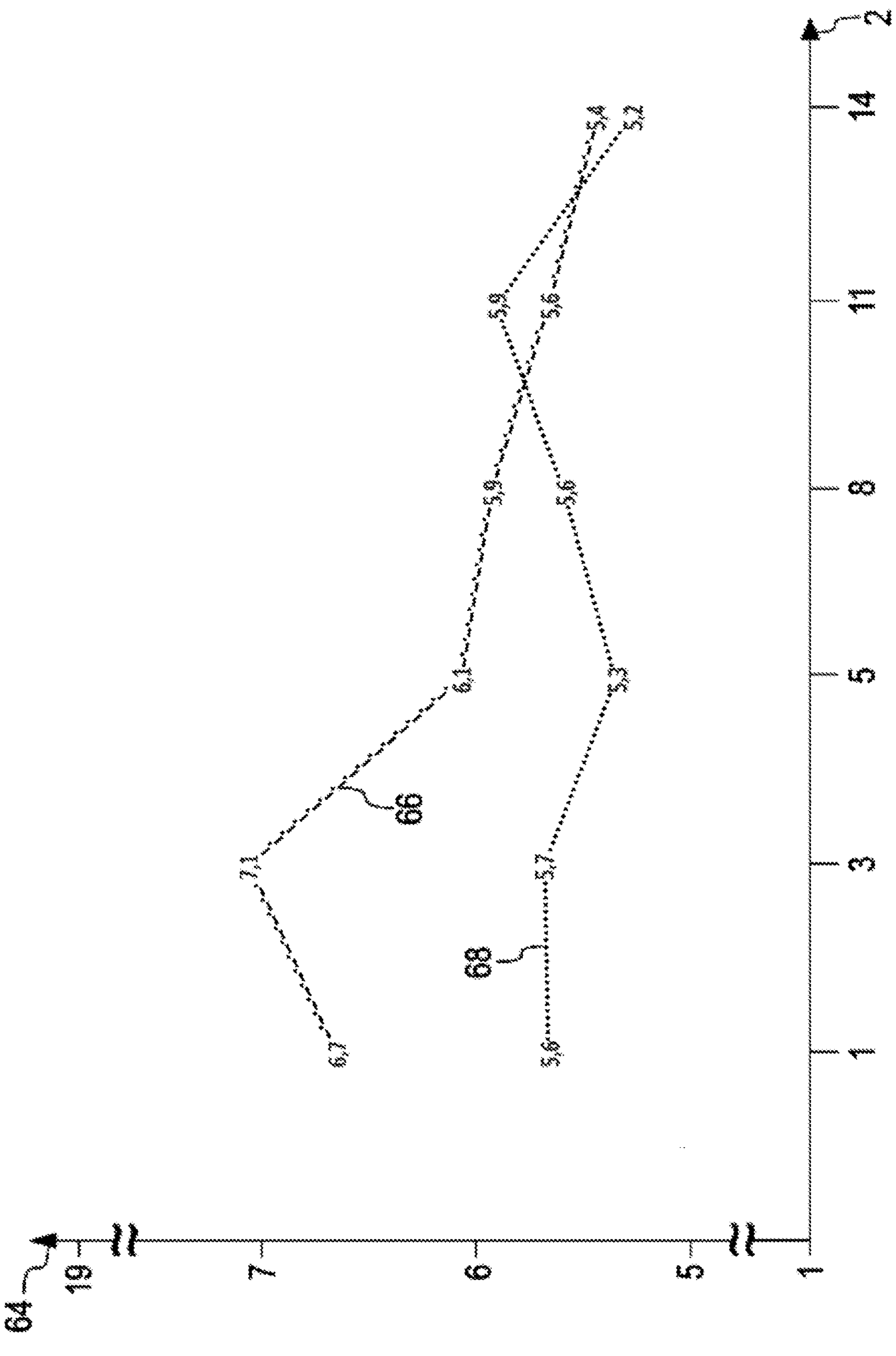
FIG. 8 is a diagram showing an evaluation of collected trial data on the "Negative-Relaxed" scale according to the Brief Mood Introspection Scale, abbreviated BMIS, 3rd edition, Feb. 26, 2019.

The values thus calculated for the subscales are plotted against time 2 in the diagrams shown in FIGS. 5 to 8 to evaluate the result. The diagram of FIG. 5 shows over time 2 on the satisfaction scale 34 (according to BMIS: "Pleasant-Unpleasant"), a chewing gum satisfaction curve 36 with the daily values for the chewing gums according to the embodiment example of the claimed composition and a tablet satisfaction curve 38 with the daily values for the tablets according to the alternative composition. The diagram of FIG. 6 shows over time 2 on the arousal scale 44 (according to BMIS: "Arousal-Calm"), a chewing gum arousal curve 46 with the daily values for the chewing gums according to the embodiment example of the claimed composition and a tablet arousal curve 48 with the daily values for the tablets according to the alternative composition. The diagram of FIG. 7 shows over time 2 on the fatigue scale 54 (according to BMIS: "Positive-Tired"), a chewing gum fatigue curve 56 with the daily values for the chewing gums according to the embodiment example of the claimed composition and a tablet fatigue curve 58 with the daily values for the tablets according to the alternative composition. The diagram of FIG. 8 shows over time 2 on the relaxation scale 64 (according to BMIS: "Negative-Relaxed"), a chewing gum relaxation curve 66 with the daily values for the chewing gums according to the embodiment example of the claimed composition and a tablet relaxation curve 68 with the daily values for the tablets according to the alternative composition.

The curves of FIGS. 5 to 8 support the result interpreted from FIGS. 1 to 4 that both compositions lower negative moods or at least keep them constant and increase positive moods. The subjects felt more alert and were more attentive.

The invention claimed is:

1. A composition comprising lavender oil as an active ingredient for medicinal use in a treatment of a concentration disorder, and a gum base comprising synthetic gum, wherein the composition comprises the gum base, and lavender oil as an active ingredient is in a concentration of 0.1 to 1 wt %, and wherein the gum base has a tensile strength between 0.25 N/mm$^2$ and 4 N/mm$^2$ for engaging the facial muscles;

wherein the lavender oil is the sole active ingredient; and wherein the lavender oil as the active ingredient is in the concentration of 0.2-0.4 wt %.

2. The composition according to claim 1, wherein the gum base comprises the synthetic gum as consistency former.

3. The composition according to claim 1, wherein the gum base comprises 0.05 to 0.5 wt % of a trace element.

4. The composition according to claim 3, wherein the trace element is zinc.

5. The composition according to claim 3, wherein the gum base comprises 0.1 wt % to 1 wt % of a salt.

6. The composition according to claim 5, wherein the salt is sodium chloride.

7. The composition according to claim 1, wherein the gum base comprises 0.05 wt % to 0.5 wt % of a vitamin B.

8. The composition according to claim 5, wherein the vitamin B comprises niacin and/or pantothenic acid.

9. The composition according to claim 5, wherein the gum base comprises 0.1 wt % to 1 wt %, of a vitamin D.

10. The composition according to claim 9, wherein the vitamin D is biotin.

11. The composition according to claim 1, wherein the gum base further comprises an acidity regulator.

12. The composition according to claim 11, wherein the acidity regulator is citric acid.

13. The composition according to claim 1, wherein the gum base comprises a sugar alcohol.

14. The composition according to claim 1, wherein the gum base comprises synthetic and/or natural gum as consistency former.

15. The composition according to claim 1, wherein the gum base comprises 0.05 to 0.5 wt % of a trace element.

16. A composition comprising lavender oil as an active ingredient for medicinal use in a treatment of a concentration disorder, and a gum base comprising synthetic gum, wherein the composition comprises the gum base, and lavender oil as an active ingredient is in a concentration of 0.1 to 1 wt %, and wherein the gum base has a tensile strength between 0.25 N/mm$^2$ and 4 N/mm$^2$ for engaging the facial muscles;

wherein the lavender oil is the sole active ingredient; and wherein the lavender oil as the active ingredient is in the concentration of 0.3 wt %.

17. The composition according to claim 16, wherein the gum base the gum base comprises 0.1 wt % of a trace element, 0.15 wt % of a vitamin B, and 0.3 wt % of a vitamin D.

* * * * *